United States Patent [19]

Green

[11] Patent Number: 5,304,170
[45] Date of Patent: Apr. 19, 1994

[54] METHOD OF LASER-INDUCED TISSUE NECROSIS IN CAROTENOID-CONTAINING SKIN STRUCTURES

[76] Inventor: Howard A. Green, 293 Temple St., #301, West Roxbury, Mass. 02132

[21] Appl. No.: 31,242

[22] Filed: Mar. 12, 1993

[51] Int. Cl.[5] ............................................ A61B 17/36
[52] U.S. Cl. ......................................... 606/9; 606/3; 128/898
[58] Field of Search ...................... 606/2, 3, 9, 13, 16; 128/898

[56] References Cited

U.S. PATENT DOCUMENTS

| | | | |
|---|---|---|---|
| 4,718,416 | 1/1988 | Nanaumi | 606/9 |
| 4,887,600 | 12/1989 | Watson et al. | |
| 5,000,752 | 3/1991 | Hoskin et al. | 606/9 |
| 5,071,422 | 12/1991 | Watson et al. | |

FOREIGN PATENT DOCUMENTS 9113652 9/1991 World Int. Prop. O. .............. 606/9

OTHER PUBLICATIONS

Gilchrest et al., "Chilling Port Wine Stains Improves the Response to Argon Laser Therapy" Feb. 1982 Plastic and Reconstructive Surgery.
"The Sebaceous Glands:Twenty-Five Years of Progress" Strauss/Pochi/Downing-The Journal of Investigative Dermatology 1976.
"The Biochemistry and Function of Stratum Corneum Lipids" Schurer/Elias-Academic Press, Inc.-Advances in Lipid Research 1991.
"Chemistry and Function of Mammalian Sebaceous Lipids" Stewart/Downing-Academic Press Inc. Advances in Lipid Research vol. 24 1991.
"Treatment of Xanthelasma Paipebrarum with the Carbon Dioxide Laser" Apfelberg/Maser/Lash/White: Dermatol. Surg. Oncology 1987.
"Selective Photothermolysis:Precise Microsurgery by Selective Absorption of Pulsed Radiation" Anderson/Parrish-American Assoc. For The Advancement of Science 1983.
"Increased Preferential Absorption in Human Atherosclerotic Plaque with Oral Beta Carotene" Prince/LaMuraglia/MacNichol-Circulation-Aug. 1988.
"A Clinical Trial of the Effects of Oral Beta-Carotene on the Responses of Human Skin to Solar Radiation" Mathews-Roth/Pathak/Parrish/Fitzpatrick/Kass/Toda/Clemens New Journal of Investigative Dermatology 1992.
"The Infiltration of Cartenoids Into Human Atherones and Xanthomas" Blankenhorn vol. 53, No. 5 1960.
"Kinetic Characteristics of Beta-Carotene Uptake and Depletion in Rat Tissue" Shapiro/Mott/Machlin-American Institute of Nutrition Mar. 1984.
"Rapid Serum Carotene Loading with High-Dose B-Carotene:Clinical Implications" Prince/Frisoli/Goetschles/Stringham/LaMuraglia-Journal of Cardiovascular Pharmacology 1991.
"Carotendermia in men with elevated carotenoid intake from foods and Beta-Carotene Supplements" Micozzi/Brown/Taylor/Wolfe-American Society for Clinical Nutrition 1988.
"Beta-Carotene accumulation in serum and skin" Prince/Frisoli-American Society for Clinical Nutrition 1993.
"Effect of Wave Length on Cutaneous Pigment Using Pulsed Irradiation" Sherwood/Murray/Kurban/Tan-Society for Investigative Dermatology Inc. 1989.

Primary Examiner—Stephen C. Pellegrino
Assistant Examiner—Sonya C. Harris
Attorney, Agent, or Firm—Richard P. Crowley

[57] ABSTRACT

A method for treating dermatological organ disorders and skin lesions in a mammal through the use of directed, pulsed laser light is described.

The dermatological disorders are characterized by an increase in concentration of potential photodynamic chemical compounds like carotenoid compounds, and especially the carotenoid beta-carotene, compared to normal skin. Pulsed dye laser light of a time and duration specific for maximal absorption by a carotenoid compound like beta-carotene is directed at the regions of carotenoid accumulation within a skin disorder. Thermal coagulation necrosis of the carotenoid-accumulating skin region results, though thermal damage to surrounding tissue is limited in amount.

13 Claims, No Drawings

METHOD OF LASER-INDUCED TISSUE NECROSIS IN CAROTENOID-CONTAINING SKIN STRUCTURES

BACKGROUND OF THE INVENTION

Skin organ disorders such as dermatological acne and xanthomas have traditionally been treated by chronic oral medications and chronic topical applications with medicated creams and by surgical techniques. However, a typical result is extensive scarring of the skin even when surgical treatment to rid the disorder is successful. No non-scarring ablative treatment is currently available.

Therefore, it is desirable to provide an effective method of dermatological treatment for skin disorders like xanthomas and acne that would eliminate the need for chronic therapy and tissue scarring. Such a method should be uncomplicated for the practitioner to use as an inoffice procedure, non-toxic, comfortable for the patient undergoing treatment, and deliverable at low cost.

SUMMARY OF THE INVENTION

The present invention relates to a method for treating disorders of organs in mammals. In particular, the invention deals with treating mammalian dermatological disorders and skin lesions in which potential photodynamic chemical compounds such as carotenoids are concentrated.

The invention comprises identifying lipid-containing and associated potential photodynamic chemical-concentrating structures, such as carotenoid-containing structures, within skin, skin components and skin lesions and exposing such structures to a directed, pulsed beam of light radiation, preferably laser light radiation, that has a duration, intensity and wavelength sufficient to be absorbed by and to cause thermal coagulative necrosis of the structure without significant damage to surrounding tissues within the skin. In a preferred embodiment of the inventive method, pulsed laser light is delivered to a targeted skin structure by means of an optical fiber directed at that structure.

Targeted structures comprises organs known to concentrate potential photodynamic chemicals such as, for example, carotenoids, in association with the presence of lipids. Carotenoids, and the carotenoid beta-carotene in particular, are known to concentrate in skin diseases such as acne and xanthomas. Affected skin structures targeted in the invention include but are not limited to sebaceous cells, xanthoma cells and stratum corneum of the skin. More particularly, targeted skin structures and skin lesions include but are not limited to eruptive, tuberous, tendenous, and plane xanthomas; xanthelasmata; xanthoma disseminatum; juvenile xanthogranulomas; nevus sebaceous; sebaceous hyperplasia, adenoma, and carcinoma; fordyces condition; sebaceoma; sebaceous glands; acne vulgaris, conglobata, and rosacea; and basal cell carcinoma with sebaceous differentiation. In the aforementioned skin structures, diseases and lesions, the carotenoid concentration is increased compared to normal skin. Potential photodynamic chemicals such as carotenoids may be further increased in concentration within an organ orally through normal diet or by the exogenous administration of a supplemental, pharmaceutically-acceptable compound, such as for example, non-toxic beta-carotene, prior to illumination by a pulsed laser beam.

In the inventive method, a pulsed beam of light radiation, preferably laser light radiation, is delivered to the potential photodynamic chemical-containing components within mammalian skin by an optical fiber directed at the targeted structure. Small optical fibers are used preferentially for small skin lesions due to their flexibility and precision. Large diameter optical fibers are preferred for targeting large skin structures and lesions because they more uniformly illuminate a larger area in a shorter period of time and thereby decrease treatment time. The optical fiber may be suspended above the skin structure and thereby have an air interface between the optical fiber and the skin. Alternatively, a fluid interface may exist between the optical fiber and the targeted skin structure. In a preferred embodiment, the optical fiber is placed directly against the skin over the defined targeted structure.

The proximal end of the optical fiber accepts a pulsed beam of light from a light source such as, for example, the flashlamp excited dye laser, an argon, argon fluoride, selenium, or doubled titanium sapphire laser. Any source of light radiation of sufficient wavelength and intensity to damage organ components may be used. In a preferred embodiment, the source of light radiation is a dye laser. A dye laser is connected to a dye source resulting in a characteristic wavelength selected for optimal absorption by potential photodynamic chemicals such as carotenoids within the skin structures. The optimal wavelength at which the laser operates, and so the type of dye used, is selected in part according to the per cent transmission characteristic of the organ after supplemental administration of a potential photodynamic chemical. For example, by illuminating the skin with a wavelength specifically absorbed by carotenoids yet below a threshold intensity level for vaporization, ionization, or fragmentation of targeted skin components, thermal energy is transferred to skin structures or lesions that have accumulated high levels of carotenoids. The result is thermal damage or necrosis of these structures. Such wavelengths are within the range of about 425–550 nanometers and more particularly about 504 nanometers. Reference is made to an absorption spectrum for beta-carotene given within the *J. Clin. Nutr.* 57: 175–181 (1993), hereby incorporated by reference.

A laser is connected proximally to a control panel to enable the user to activate and deactivate the laser, to vary radiant energy per pulse, and to vary the pulse repetition rate of the laser beam.

Laser radiant energy per pulse is related directly to laser intensity and is kept as low as possible to achieve maximum thermal damage in an organ structure having accumulated potential photodynamic chemicals such as carotenoids like beta-carotene, and minimum thermal damage in normal, non-photodynamic chemical-concentrating surrounding tissues. Optimal radiant energy per pulse ranges from about 0.10 joules per square centimeter to 10 joules per square centimeter.

Laser pulse duration is inversely proportional to laser intensity. Laser pulse duration varies according to target diameter in order to maximize selective thermal denaturation of a targeted organ structure for example, $10^{-3}$ to $10^{-9}$ seconds. In a preferred embodiment, shorter pulses measured within a nanosecond or microsecond range are useful for selective thermal damage to small diameter carotenoid-concentrating skin structures that have shorter thermal relaxation or recovery times. Longer pulses such as, for example, pulses of microsecond or millisecond duration, are useful for selective thermal damage to large carotenoid-concentrating skin structures that have longer thermal relaxation or recovery times. Such longer thermal relaxation times are associated with larger organs such as, for example, sebaceous glands and xanthomas. Laser pulse durations in a preferred embodiment range from about 250 nanoseconds to about 10 milliseconds.

Both laser pulse duration and laser radiant energy content combine to produce laser intensity that emanates from the distal end of the optical fiber. This intensity must be low enough to minimize formation of a tissue-damaging, fragmenting shockwave in and around the targeted organ structure as well as to minimize tissue vaporization or explosive ablation. However, laser intensity must be greater than a threshold thermal damage level for, for example, skin components that contain accumulated carotenoid pigments in order to achieve thermal coagulative necrosis within that structure. When laser intensity reaches a threshold level of thermal damage to, for example, a skin structure, a change in coloration of the targeted skin structure is observed.

The invention will be described for the purposes of illustration only in connection with certain embodiments; however, it is recognized that those skilled in the art may make various modifications, changes, additions, and improvements to the certain embodiments, all falling within the spirit and scope of the invention.

DESCRIPTION OF THE EMBODIMENTS

A method of laser-induced tissue necrosis in a potential photodynamic chemical-containing structure in a mammalian organ is described.

In the preferred embodiment, a skin disorder is identified by an increased concentration of a potential photodynamic chemical compound, such as the carotenoid beta-carotene, within its structure when compared to normal skin tissue. Prior to laser therapy, the beta-carotene content of skin structural components and skin lesions to be treated may be increased by the exogenous supplemental administration of pharmaceutically-acceptable, non-toxic beta-carotene or by diet. Heating of skin structural components by laser energy is initiated only at sites of optical absorption by the beta-carotene compound.

Next, the identified skin structure is illuminated by the distal portion of an optical fiber. The size of the optical fiber is chosen to accomodate the diameter of the targeted skin tissue, either a small optical fiber for a target of small diameter or a large optical fiber for a large diameter target. The proximal portion of the optical fiber is attached to receive a pulsed beam of light radiation from a laser source, particularly a laser source connected to a dye source selected for production of a wavelength characteristic for optimal absorption by the beta-carotene carotenoid compound within the skin.

The laser is also connected to a control panel that allows a user to activate and deactivate the laser and to vary both pulse repetition rate and radiant energy levels. Wavelengths of optimal absorption of laser light by carotenoid compounds range from about 425 to 550 nanometers, and more particularly is about 504 nanometers.

The duration of each laser light pulse delivered is shorter than the time required for cooling of the target skin components in order to maximize the selective thermal damage to the target tissue structure. Selective damage to carotenoid-containing skin components occurs with little or no effect on surrounding tissue integrity. Pulse duration varies with target tissue diameter. Shorter pulses such as those in a nanosecond and microsecond range are used for small diameter target tissues like sebaceous or xanthoma cells. Longer pulses within microsecond and millisecond ranges are used for larger diameter target tissues such as sebaceous glands and xanthomas. Optimal pulse durations in a preferred embodiment with a pulsed dye laser range from about 250 nanoseconds to 10 milliseconds.

Radiant energy per pulse of laser light is maintained as low as possible to maximize the amount of thermal damage done in carotenoid-laden tissues as well as to minimize thermal damage to tissues that do not concentrate carotenoids. Radiant pulse energy in the preferred embodiment ranges from about 0.10 joules per square centimeter to 10 joules per square centimeter depending on the type and size of target tissue.

When laser intensity directed at a target tissue has caused a threshold thermal coagulative necrosis within a target skin structure, a change in skin coloration is observed. No eruption through the skin occurs and, consequently, scarring is avoided.

As a representative example, a person with acne is placed on a daily regimen of 120 milligrams beta-carotene in its diet for 10 to 14 days. Beta-carotene administration is then discontinued, and the person has an optical fiber placed directly on his skin over a targeted area of acne. A pulsed dye laser light having a radiant energy of about 1 joule per square centimeter and a wavelength of about 504 nanometers is delivered to that area for a duration of about 2 milliseconds, at which time a distinct change in skin coloration in the targeted area is noted even though no surface breaks in the skin appear.

What is claimed is:

1. A method for treating dermatological organ disorders and skin lesions in a mammal which method comprises:
    a) identifying an area of skin within a region of mammalian skin, which area is characterized by cells of increased carotenoid compound concentration compared to the region of mammalian skin;
    b) directing a pulsed laser light beam at said area of skin; and
    c) exposing the said area of skin to said pulsed laser light beam of selected pulse duration and a wavelength of laser light between about 425 and 550 nanometers, and wherein the pulsed laser light beam contains radiant energy of between about 0.10 joules per square centimeter and 10 joules per square centimeter to cause thermal coagulation necrosis within the said cells of said area of skin and thereby to treat the dermatological organ disorder and skin lesion within said area of skin.

2. The method of claim 1 wherein the carotenoid compound is beta-carotene.

3. The method of claim 1 which includes increasing the concentration of the carotenoid compound by supplemental administration to the mammal of a pharmaceutically-acceptable form of said carotenoid compound prior to directing and exposing the said area to the light beam.

4. The method of claim 3 which includes increasing the concentration of the carotenoid compound in said cells through diet.

5. The method of claim 1 which includes directing the laser light beam to the area of skin by means of an optical fiber.

6. The method of claim 1 which includes pulsing the laser light beam between about 250 nanoseconds to 10 milliseconds.

7. The method of claim 1 wherein the laser light beam emanates from a pulsed dye laser.

8. The method of claim 1 wherein the pulsed laser light beam has a wavelength of about 504 nanometers.

9. The method of claim 1 which includes identifying when thermal coagulation necrosis occurs in said area of skin by a change in skin coloration in said area.

10. The method of claim 1 wherein the disorder and skin lesions are selected from this group consisting of eruptive, tuberous, tendenous, and plane xanthomas; xanthelasmata; xanthoma disseminatum; juvenile xanthogranulomas; nevus sebaceous; sebaceous hyperplasia, adenoma, and carcinoma; fordyces condition; sebaceoma; sebaceous glands; acne vulgaris, conglobata, and rosacea; and basal cell carcinoma with sebaceous differentiation.

11. The method of claim 1 wherein the said cells are sebaceous cells.

12. The method of claim 1 wherein the said cells are xanthomatous cells.

13. A method for treating dermatological skin disorders in a mammal which method comprises:
  a) identifying an area of skin within a region of mammalian skin, which area is characterized by a concentration of a beta-carotene compound;
  b) increasing the concentration of the beta-carotene compound within said area of skin by administration of a pharmaceutically-acceptable form of said carotene compound to the mammal;
  c) directing a beam of pulsed laser light radiation having an energy of between about 0.10 and 10 joules per square centimeter and a wavelength of about 504 nanometers from a pulsed dye laser at said area of skin; and
  d) exposing said area of skin to the beam of pulsed laser light radiation for a sufficient period of time to cause thermal coagulation necrosis within the area of skin and thereby to treat the skin disorder.

* * * * *